United States Patent [19]

Wunderle, geb. Rudigier et al.

[11] Patent Number: 4,859,185
[45] Date of Patent: Aug. 22, 1989

[54] DENTAL CAP FOR USE IN MAKING JACKET CROWNS

[76] Inventors: Anita Wunderle, geb. Rudigier, Lorenz-Wenk-Weg 22, 7880 Bad Säckinghen 11; Michael Frank; Dieter Schössow, both of Basler Str. 8, 7889 Grenzach-Whylen, all of Fed. Rep. of Germany

[21] Appl. No.: 188,529

[22] Filed: Apr. 29, 1988

[30] Foreign Application Priority Data

May 6, 1987 [DE] Fed. Rep. of Germany ....... 3715096

[51] Int. Cl.4 .............................................. A61C 5/08
[52] U.S. Cl. .................................. 433/222.1; 433/218
[58] Field of Search .................... 433/222.1, 223, 218, 433/227, 208, 207; 264/19, 20

[56] References Cited

U.S. PATENT DOCUMENTS

| | | | |
|---|---|---|---|
| 1,444,436 | 2/1923 | Teeter | 433/223 |
| 1,609,550 | 12/1926 | Jaques | 433/218 |
| 1,711,402 | 4/1929 | Berger | 433/223 |
| 2,283,786 | 5/1942 | Brenner | 433/222.1 |
| 2,700,822 | 2/1955 | Infante | 433/222.1 |
| 4,492,579 | 1/1985 | Shoher et al. | 433/222 |

Primary Examiner—John J. Wilson
Attorney, Agent, or Firm—Armstrong, Nikaido, Marmelstein, Kubovcik & Murray

[57] ABSTRACT

A dental cap for the veneer of a jacket crown comprising a noble metal foil in substantially frusto-conical shape, which starting from a substantially circular foil piece is formed by folding the outer region in the direction towards the axis of rotation to form overlappings, the outer region of the foil piece being divided into flaps and the overlapping regions being joined inseparably together. For dividing the outer region two different types of cuts are made from the outer edge in the direction towards a surface area disposed in the center and as a result of said cuts the dental cap is completely closed in the side wall region by overlappings there.

20 Claims, 1 Drawing Sheet

DENTAL CAP FOR USE IN MAKING JACKET CROWNS

BACKGROUND OF THE INVENTION

1. Field of the Invention

The invention relates to a dental cap for use as a carrier for the veneer of a jacket crown.

2. Description of the Prior Art

A dental cap is already known of a noble metal foil of substantially cylindrical or cylindrical-frusto-conical shape, which starting from a circular foil piece is formed by folding over the outer region thereof in the direction towards the axis of rotation of the foil piece to form mutual overlappings, the overlapping regions being joined undetachably to each other (see US Pat. No. 4,492,579).

Except for the centre region of the circular foil piece this cap is prefolded in harmonica manner and at the same time folded over in the direction towards the axis of rotation of the foil piece so that the outer region of the cap has an appearance corresponding substantially to a half-opened umbrella. The cap thus formed is then placed by the dental technician on a tooth stump model corresponding to the peculiarities of a patient, pressed in the central region radially against the tooth stump model and held fixed in this manner with simultaneous rolling of the harmonica pleats of the outer region against the outer surface of the tooth stump model, this corresponding substantially to the further closing of an umbrella and wrapping it round the umbrella stick. With a view to exact adaptation of the dental cap to the tooth stump model, the operation of folding the harmonica pleats together and rolling them against the outer surface of the tooth stump model must be carried out very accurately. Also, this work can be done only manually by the dental technician and is thus relatively time-intensive and therefore expensive. In addition the rolling of the foil against the tooth stump model requires great skill on the part of the dental technician to avoid unintentional cross folds or the like resulting in local irregularities in the wall thickness of the cap, which cannot be equalized even on subsequent insertion of the rolled cap into a so-called swager. Such unintentional transverse folds can contain air inclusions which cannot be filled with liquid gold in the subsequent treatment in a flame to obtain an inseparable mutual fixing of overlapping regions of the foil.

With a view to a more rapid and more economical producability starting from the dental cap described above, and in particular to avoid excessive demands on the skill of the operating dental technician, it has elsewhere already been proposed to divide the outer region of the foil piece into at least two wing-shaped flaps, adjacent flaps being connected together at a distance from the centre of the foil piece corresponding to at least half the diameter of the cap upper side. Admittedly, the dental cap formed in this manner can be made economically and simply and indeed without particular skill on the part of the dental technician working it; since, however, the end points of the cuts bordering two adjacent flap sides coincide, i.e. the two cuts terminate at a single point, there is a danger when folding the flaps over that small areas of the dental cap are left open. These open areas, however small they may be, involve the risk that they cannot be satisfactorily sealed on mutual inseparable fixing of the overlapping regions by melting on dusted gold powder or the gold of the foil itself.

SUMMARY OF THE INVENTION

The invention is thus based on the problem of further developing the dental cap of the type referred to at the beginning in such a manner that when the flaps are bent over no open areas remain and thus any danger of passage of molten gold is eliminated.

The invention therefore proposes in a dental cap for use as a carrier for the veneer of a jacket crown, said cap consisting of a noble metal foil, in particular a noble metal composite foil, in substantially frusto-conical shape, which is formed from a substantially circular foil piece by folding over the outer region thereof in the direction towards the axis of rotation of the foil piece to form mutual overlappings, for which purpose the outer region of the foil piece is divided into at least two wing-shaped flaps and the flap regions are joined undetachably to each other, the improvement wherein for dividing the outer region of the foil piece into flaps cuts are made from the outer edge thereof in the direction towards a rectangle or square which is imagined in the centre thereof and which corresponds to the shape of the occlusal face of a tooth stump model to be crowned and has at the most the same magnitude as said face, the first cut—cut of the first type—meeting to form a first flap the sideline of the rectangle or square at a small distance from the adjacent corner of said rectangle or square, whilst to form the adjacent flap the adjacent cut—cut of the second type—meets the first cut at an appreciable distance from the meeting point of the first cut with the rectangle or square side line in the direction towards the outer edge of the foil piece, the two cuts beginning at the outer edge of the foil piece at such a distance from the centre perpendicular of the rectangle or square side line belonging to the respective flaps, which distance is substantially as great as the length of said side line, and the individual flaps being folded over in the direction towards the axis of rotation of the foil piece about a line joining the two end points of their cuts.

Advantageous further developments are set forth in the subsidiary claims.

The construction according to the invention does not differ in any way as regards the demands made of the skill of the dental technician in making the cut foil piece from the cutting of the dental cap proposed elsewhere and discussed above. It is merely necessary to make the cuts in a different manner, i.e. according to the invention. The novel art of the cut pieces ensures that on proper folding of flaps to form the overlapping regions no openings at all are present in the side wall region of the cap, the flaps overlapping each other mutually completely so that if desired a double-walled configuration is also possible there. The configuration of the cuts according to the invention also ensures that the starting point of the mutual overlapping of the flaps lies in the region of the cap which is to be associated with the occlusal face of a tooth stump model. The starting point, itself not closable, of the mutual overlapping of the flaps can easily be closed with a melting on of gold powder or a melting on of foil gold, without the molten gold passing through the starting point of the overlapping and in particular forming an obstruction to the cap upon subsequent fitting thereof on the original tooth stump. Due to the flap formation originating from the cuts it is not necessary either to provide any preliminary embossings of the fold lines of any type whatever. Thus, the configuration according to the invention also simplifies the making of the dental cap as such because it is readily possible to bend the flaps over in the direction towards the axis of rotation of the foil piece and at the same time effect mutual overlapping of the flaps. The dental cap made in this manner need only be placed on a tooth stump model and then without further manual intermediate work introduced together with the tooth stump model into a swager where with a single strong impact in the axial direction of the tooth stump model the dental cap can be formed to the shape with which, for mutual inseparable fixing of the flaps of the foil piece, it is exposed to a flame to obtain by melting the gold an extremely stable dental cap which is absolutely sealed in its side wall and which is then available for the subsequent veneering with porcelain or plastic.

With the configuration according to the invention practically any special manual work on the part of the dental technician is eliminated and in addition no particular skill required of the technician; as a result the working time for making the finished dental cap is considerably reduced so that the production of a finished jacket crown of at least the same quality as hitherto is made considerably cheaper.

Also, the danger of formation of transverse folds during the making of the dental cap is eliminated and in this respect the quality of a jacket crown made using the dental cap according to the invention is therefore also improved. By corresponding arrangement of the cuts, which, because they meet each other, form a cutout, it is moreover possible to obtain a practically absolute uniformity of the wall thickness in the side wall region of the finished dental cap.

BRIEF DESCRIPTION OF THE DRAWINGS

The dental cap according to the invention will be described hereinafter in further detail with reference to the drawings, wherein.

DESCRIPTION OF THE PREFERRED EMBODIMENTS

Figure 1:
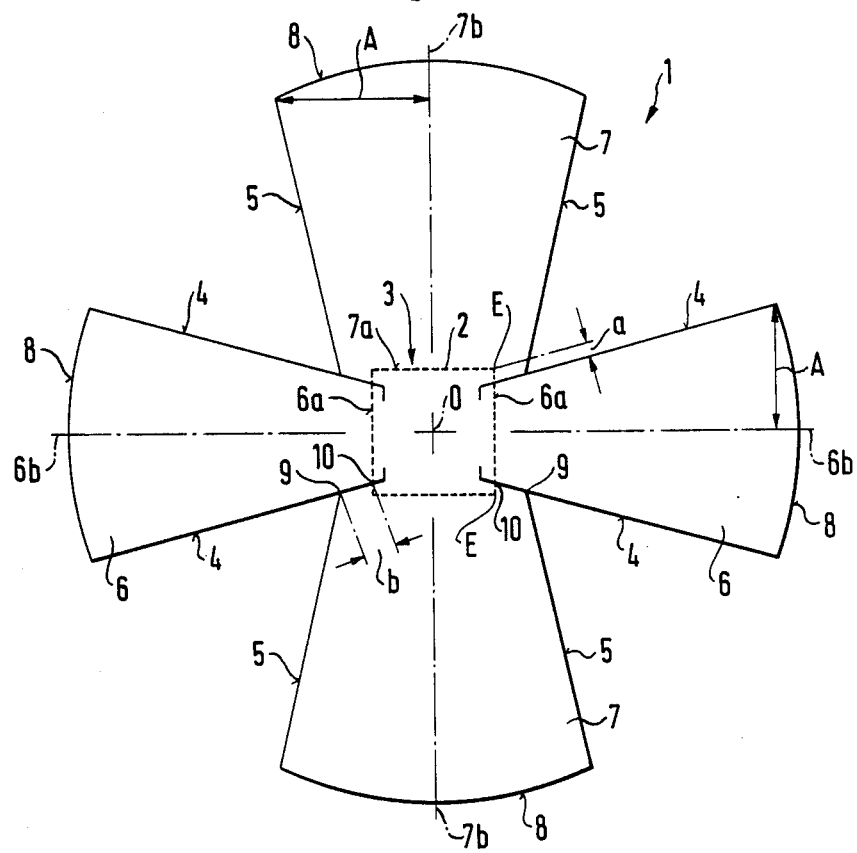
FIG. 1 is a plan view of a cut piece or blank of an originally substantially circular foil piece for making a dental cap according to the invention having four flaps and FIG. 2 is a plan view of a cut piece of a foil piece for making a dental cap according to the invention having only two flaps.

FIG. 1 shows in plan view the cut piece or blank 1 for making a dental cap according to the invention. In the centre of the blank 1 by dot lines 2 a square is shown which has in its shape substantially the form of the occlusal face of a tooth stump model to be crowned. The square 3 is at the same time somewhat smaller in size than said occlusal face.

By forming a total of four cuts 4 and likewise four cuts 5, two pairs of diametrically opposite flaps 6 and 7 are formed.

The cuts 4 and 5 each originate from the outer edge 8 of the originally circular foil piece. The cuts 4 for the flaps 6 are led up to the respective associated side line 6a of the square 3 and terminate there a small distance a from the corner E of the square 3. Likewise, the cuts 4 start at the outer edge 8 at a distance A from the centre perpendicular 6b of the associated side line 6a of the square 3. This distance A corresponds substantially to the length of the side line 6a.

Analogously, the cuts 5 likewise begin at a distance A from the centre perpendicular 7b of the side line 7a of the square 3. The cuts 5 terminate however on the cuts 4 (meeting point 9), at a distance b from the meeting point 10 of the cuts 4 with the side lines 6a of the square 3. The distance b should be about 3 mm but not longer than the side line.

FIG. 1 shows at the same time a further development of the dental cap according to the invention in which the cuts 4 are extended beyond their meeting points 10 in their own direction and then substantially parallel to the associated side lines 6a of the square 3 in the direction towards the centre perpendicular 6b. The two extension portions are relatively small and at the most 2 mm; as a rule they will be dimensioned with regard to the length of the side line and should be about 3/10 of said length.

The distance a of the intersection or meeting points 10 of the cuts 4 from the corners E of the square 3 should be as a rule 1/10 of the length of the side line 6a of the square 3 but at least 0.5 mm and at the most 1.5 mm.

To form the cap-shaped configuration firstly the flaps 6 formed by cuts 4 are folded over in the direction towards the axis of rotation 0 of the foil piece 1, about an imaginary line connecting the ends points of their cuts 4.

Thereafter the flaps 7 formed by cuts 5 are folded over in the same direction. The edge-side regions of the flaps 7 then overlap the edge-side regions of the flaps 6 and this overlapping becomes increasingly larger with the increase of the folding over of the flaps 6 and 7. The overlapping starts at the end points 4a of the cuts 4. Admittedly, no overlapping is present at the end point 4a of the cuts 4 because this is not possible; however, this is not a disadvantage for the dental cap because this punctiform lack of overlapping lies in the region of the occlusal face and can easily be sealed in the usual manner by melting on gold powder or gold foil. In the entire side region the dental cap is sealed by overlapping of its flaps 6 and 7.

The folding over and tight application of the flaps 6 and 7 onto a tooth stump model can easily be carried out in a swager in which the model is incorporated practically as anvil and in which from above with a hefty blow a resilient punch with a central cutout for receiving the tooth stump model with dental cap can be brought down onto the latter.

Of course, it is also possible to make the flaps 6 and 7 in identical manner; they will then be asymmetrical with respect to their centre perpendiculars 6b and 7b. In this case one half of the flaps 6 and 7 has the appearance shown in FIG. 1, whilst the other half of the flaps 6 and 7 corresponds to the half of the flaps 7 and 6 according to the illustration of FIG. 1. It must, however, be ensured that cuts 4 and 5 always alternate, as is readily possible because the corresponding configuration of the two halves of each flap in this case requires provision of a cut 4 and a cut 5 for each flap.

Figure 2:
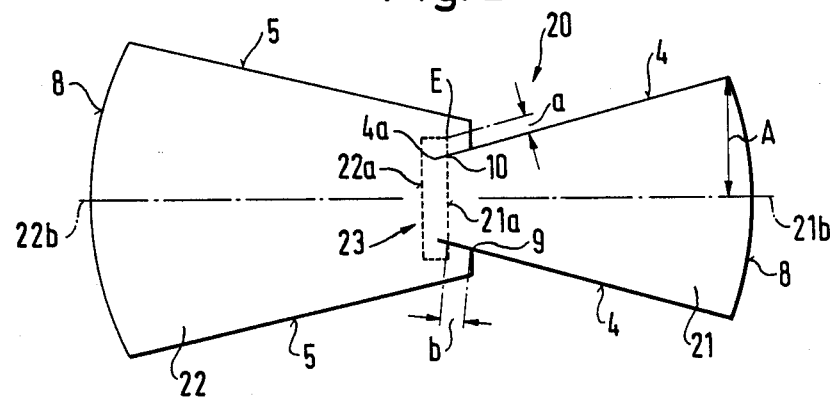

FIG. 2 shows basically the same illustration as FIG. 1 with a foil blank 20 for use for a tooth stump of pronounced rectangular shape, i.e. for example a tooth stump of a front tooth. In this case a total of only two flaps are to be formed by correspondingly placed cuts, said flaps 21 and 22 being diametrically opposed and each starting at the longitudinal sides 21a and 22a of the rectangle 23.

This embodiment corresponds to the embodiment of FIG. 1 if it is imagined in the latter that instead of the one flap 6 opposite the other flap 6 a flap 7 is provided and otherwise the two flaps 7 are omitted and at the same time the square 3 is made smaller by shortening the side line 7a to give a rectangle 23 according to FIG. 2.

In the embodiment of FIG. 2 the cuts 4 are lengthened only in their own direction but not at the same time parallel to the associated side line 21a of the rectangle 23. Nevertheless, in this case as well it is readily possible to obtain a mutual overlapping of the flaps 21 and 22 so that at worst the overlapping is lacking only at the ends points 4a of the cuts 4 which are in the region of the occlusal face of the tooth stump model.

The configuration according to the invention provides a dental cap as carrier for a veneer of a jacket crown which has astonishingly high dimensional stability, a wall thickness which is absolutely uniform and can be reproduced at any time and which otherwise is extremely economical, in particular as regards the labour costs or also as regards the material costs and in particular is cheaper than any dental cap made by casting technology. At the same time, any danger of lack of overlapping in the side region of the cap is eliminated.

As veneer materials, of course apart from porcelain, the plastics usually employed in dental ceramics can also be used.

The mutual fixing of the flaps 4 and 6 or 21 and 22 in their overlapping regions can also be done by cold welding instead of gold melting and such a welding can moreover sometimes be carried out even simultaneously with the folding over of the flaps in the direction towards the axis of rotation of the foil piece.

We claim:

1. A noble metal sheet for forming a dental cap comprising at least one first flap and at least one second flap connected at one end of each of said flaps, each flap having at least two sides, the width of said first flap being substantially larger than that of said second flap, at least said first flap being adapted to provide a quadrilateral region substantially identical to a quadrilateral occlusal face of a model of a tooth stump to be crowned at said one end thereof, each of said two sides of said second flap intersecting with each of said two sides of said first flap and further extending toward said quadrilateral region in order to form a first cut, wherein said noble metal sheet is placed upon said tooth stump model, then said both sides of said first flap are folded in a manner such that said both sides of said first flap overlap covering said both sides of said second flap.

2. The noble metal sheet of claim 1, wherein each of said flaps has a periphery at a side opposite to said one end, said periphery having a shape of an arc.

3. The noble metal sheet of claim 1, wherein said first and second flaps are a pair of said first flaps and a pair of said second flaps respectively in order to form a substantially cross shape.

4. The noble metal sheet of claim 3, wherein said quadrilateral region is a square.

5. The noble metal sheet of claim 3, wherein said four flaps extend symmetrically and two flaps of each pair extend in opposite directions and are identical in shape and size.

6. The noble metal sheet of claim 3, wherein said pair of second flaps are firstly folded upon said tooth stump model and said pair of first flaps are secondly folded covering both sides of said second flaps.

7. The noble metal sheet of claim 6, wherein said second flap is firstly folded upon said tooth stump model and then said first flap is secondly folded covering both sides of said second flap.

8. The noble metal sheet of claim 1, wherein the distance between one of said first cuts and an adjacent corner of said quadrilateral region is about one tenth of a length of a side line of said quadrilateral region.

9. The noble metal sheet of claim 8, wherein said distance is from 0.5 to 1.5 mm.

10. The noble metal sheet of claim 1, wherein said first cut extends from a first meeting point intersecting with one of said sides of said first flap to a second meeting point intersecting with a side line of said quadrilateral region, the distance between said first and said meeting points is at least 3 mm and at maximum said length of said side line.

11. The noble metal sheet of claims 1 or 10, wherein said first cut further comprises a second cut extended into the inside of said quadrilateral region.

12. The noble metal sheet of claim 11, wherein said second cut further comprises a third cut extending from said second cut.

13. The noble metal sheet of claim 12, wherein said third cut is in parallel with said side line of said quadrilateral region.

14. The noble metal sheet of claim 13, wherein each length of said second and third cut is about three tenths of the length of said side line.

15. The noble metal sheet of claim 14, wherein said length is at maximum 21 mm.

16. The noble metal sheet of claim 1, wherein said first and second flaps form a single pair of said first and second flaps, each flap extending in opposite direction such that said two flaps are diametrically opposed to each other.

17. The noble metal sheet of claims 16, wherein said quadrilateral region is a rectangle.

18. The noble metal sheet of claim 16, wherein said first and second flaps are asymmetrical.

19. The noble metal sheet of claim 18, wherein said second flap is firstly folded upon said tooth stump model and said first flap is secondly folded covering both sides of said second flap.

20. A process for producing a dental cap from a noble metal sheet having at least one first flap and at least one second flap connected at one end thereof, each flap having at least two sides, the width of said first flap being substantially larger than that of said second flap, each of said two sides of said second flap intersecting with each of said two sides of said first flap and further extending into said first flap in order to form a cut, said process comprising the steps of;

placing said noble metal sheet upon a tooth stump model;
folding said at least one second flap of said noble metal sheet over said tooth stump model;
folding said at least one first flap in a manner such that both sides of said first flap overlap cover both sides of said second flap; and
connecting said flaps together.

* * * * *